United States Patent [19]
Yamamoto et al.

[11] Patent Number: 5,331,166
[45] Date of Patent: Jul. 19, 1994

[54] DENTAL X-RAY IMAGE DETECTING DEVICE WITH AN AUTOMATIC EXPOSURE FUNCTION

[75] Inventors: Koei Yamamoto; Kazuhisa Miyaguchi; Norio Takahashi, all of Shizuoka; Takao Makino; Keisuke Mori, both of Kyoto, all of Japan

[73] Assignees: Kabushiki Kaisha Morita Seisakusho, Kyoto; Hamamatsu Photonics Kabushiki Kaisha, Shizuoka, both of Japan

[21] Appl. No.: 964,431

[22] Filed: Oct. 21, 1992

[30] Foreign Application Priority Data

Oct. 25, 1991 [JP] Japan .................................. 3-306974
Oct. 25, 1991 [JP] Japan .................................. 3-306975

[51] Int. Cl.⁵ .......................... A61B 6/14; G01T 1/20
[52] U.S. Cl. .......................... 250/370.11; 250/370.09; 250/368; 378/97; 378/38
[58] Field of Search ............... 378/96, 97, 16, 38, 378/39, 40, 168, 191; 250/368, 367, 370.09, 370.11, 370.07, 370.06

[56] References Cited

U.S. PATENT DOCUMENTS

| | | | |
|---|---|---|---|
| 3,622,785 | 11/1971 | Irwin et al. | 378/191 X |
| 4,160,997 | 7/1979 | Schwartz et al. | 378/191 X |
| 4,210,812 | 7/1980 | Ando et al. | 378/191 X |
| 4,639,943 | 1/1987 | Heinz et al. | 378/96 |
| 4,739,168 | 4/1988 | Aoki | 378/97 X |
| 4,987,307 | 1/1991 | Rizzo et al. | 378/191 X |
| 5,008,547 | 4/1991 | Molteni et al. | 250/368 |
| 5,138,166 | 8/1992 | Makino et al. | 250/368 |

FOREIGN PATENT DOCUMENTS

| | | | |
|---|---|---|---|
| 129451 | 12/1984 | European Pat. Off. | 378/38 |
| 59-91383 | 5/1984 | Japan | 378/97 |
| 1-253682 | 10/1989 | Japan | 250/368 |
| 1-276597 | 11/1989 | Japan | 378/38 |

*Primary Examiner*—Constantine Hannaher
*Assistant Examiner*—Edward J. Glick
*Attorney, Agent, or Firm*—Koda and Androlia

[57] ABSTRACT

A medical X-ray image detecting device arranged such that an X-ray image sensor comprising an x-ray fluorescent element, a solid-state image pickup device and a plurality of optical fiber bundles for optically connecting the fluorescent surface of the X-ray fluorescent element to the image pickup surface of the image pickup device, is housed in an outer casing, the medical image detecting device being characterized in that it further comprises an X-ray intensity detecting element disposed in the casing adjacent to the X-ray fluorescent element. Clear X-ray images with a constant blackening degree can be obtained by controlling X-ray radiation time using the X-ray dose calculated by integrating the X-ray intensity output from the X-ray intensity detecting element with respect to X-ray exposure time.

4 Claims, 4 Drawing Sheets

DENTAL X-RAY IMAGE DETECTING DEVICE WITH AN AUTOMATIC EXPOSURE FUNCTION

BACKGROUND OF THE INVENTION

1. Field of the Invention

The present invention relates to a medical X-ray image detecting device, more particularly, a compact dental X-ray image detecting device inserted and used in a mouth to photograph teeth.

2. Prior Art

An X-ray photographing system for taking photographs in a mouth, wherein X-rays penetrated a tooth section in a mouth are converted into an optical image on the fluorescent surface in a compact X-ray image detecting device disposed behind the tooth section in the mouth and the optical image is projected to the image pickup surface of a solid-state image pickup device such as a CCD device via a plurality of glass fiber bundles, then the optical image is converted into a digital signal and reproduced on a monitor display, has become to be used for dental treatment.

In a conventional intra-oral (inside-mouth) X-ray radiography system, the position of an X-ray source for irradiating X-rays is set to a target tooth section and a compact X-ray image detecting device is set behind the tooth section. The X-ray tube voltage and current of the X-ray source are then set depending on the conditions of the photographing target section, the size and other factors of a patient by the operator of the photographing system. After these settings, X-rays are irradiated during a specific radiation period predetermined by the X-ray tube voltage and current.

The X-rays irradiated from the X-ray source penetrate the tooth section (target object to be photographed) and are converted into an optical image having a brightness proportionate to the dose of penetrated X-ray radiation to the fluorescent surface on an X-ray fluorescent element. The X-rays which have penetrated the X-ray fluorescent element are not only unnecessary but also harmful to a human body if the dose of exposure increases. In addition, the unnecessary X-rays sometimes cause adverse effects to the CCD device. It is therefore necessary to take countermeasures to prevent the adverse effects of the X-rays.

In addition, it is known that a conventional X-ray image detecting device adopts a method of projecting contracted optical images to the image pickup surface of a CCD device by processing the optical input or output surfaces of a plurality of glass fiber bundles for transmitting optical images so that the input or output surfaces obliquely intersect the cores of the filaments of the glass fiber bundles. As another conventional X-ray image detecting device, the image pickup surface of a CCD device is arranged parallel to the X-ray direction or disposed in a container away from an X-ray penetration area behind the fluorescent surface of a fluorescent element to avoid the adverse effects of X-rays on the CCD device (Laid-open Patent Application No. 2-249537).

As described above, when such conventional methods are used, wherein the CCD device's exposure period for the optical image on the fluorescent surface formed by the X-rays penetrated the tooth section is determined after the X-ray radiation conditions of the X-ray generator are determined according to the experience of an operator, the blackening degree of the X-ray image formed on the monitor display is not constant and the quality of the image changes at each photographing time, occasionally preventing image quality required for diagnosis from being obtained. As a result, rephotographing may frequently be required. This takes longer time for dental diagnosis and increases the dose of X-ray exposure to a patient, causing adverse effects.

The above-mentioned conventional device wherein the glass fiber bundles have surfaces obliquely intersecting the cores of the fiber filaments is conveniently used to contract an image of a target object projected to the fluorescent surface. However, the device lowers the resolution of the X-ray image reproduced, and is thus not necessarily suited for dental treatment.

In addition, until the X-rays reach the fluorescent surface from the X-ray source, a part of the X-rays is scattered when penetrating the inside of a target object such as a tooth tissue, generating scattered X-rays with low energy. Since the CCD device also senses X-rays with low energy of several keV or less and generates an electric signal, the X-ray image picked up by the CCD device and reproduced on the monitor display is subjected to external disturbance from the tooth tissue for example and the clearness of the image is lowered. This kind of scattering of X-rays cannot be avoided even when the CCD device is disposed in the detecting device to try to avoid the X-rays generated straight from the X-ray source as described above. As a result, the scattered X-rays enter the CCD device and disturb the image signal.

Furthermore, in the cases of the conventional X-ray image detecting devices, the X-rays penetrated the CCD device to the backside thereof is irradiated to a human body. This radiation of X-rays must be prevented.

SUMMARY OF THE INVENTION

It is therefore a purpose of the present invention to provide a medical X-ray image detecting device with an automatic exposure adjustment function capable of obtaining X-ray images with superior clearness and resolution by lowering as much as possible or eliminating unnecessary scattered X-ray radiation which causes adverse effects on a human body and CCD device.

The above-mentioned purpose of the present invention can be achieved by using a medical X-ray image detecting device arranged such that an X-ray image sensor comprising an X-ray fluorescent element, a solid-state image pickup device and a plurality of optical fiber bundles for optically connecting the fluorescent surface of the X-ray fluorescent element to the image pickup surface of the image pickup device, is housed in an outer casing, wherein the medical X-ray image detecting device further comprises an X-ray intensity detecting element disposed in the casing adjacent to the X-ray fluorescent element.

In this X-ray image detecting device, the X-ray intensity detecting element should preferably be secured to the top side of the fixture substrate of the solid-state image pickup device thereof, on which the solid-state image pickup device is mounted, or secured to the bottom side of the fixture substrate.

The X-ray intensity detecting element is connected to a control unit including an integrating circuit and a setting value comparison circuit. With the control unit, the integrating circuit outputs an X-ray dose signal obtained by integrating the output of the X-ray intensity detecting element during an X-ray radiation period, and the comparison circuit compares the value of the output signal with a preset X-ray dose used to obtain the best X-ray image quality. When the value of the X-ray dose signal becomes equal to the preset X-ray dose, the X-ray tube current of the X-ray source is shut off.

In the case of the medical X-ray image detecting device of the present invention, the cores of the filaments of the glass fiber bundles should preferably be joined nearly perpendicular to the fluorescent surface of the X-ray fluorescent element thereof. Furthermore, at least the front section on the X-ray incident side of the container thereof made of a soft X-ray absorbing material is adopted.

When the medical X-ray image detecting device of the present invention is used, the optical image on the fluorescent surface of the X-ray fluorescent element formed by the X-ray penetrated a target object is projected to the image pickup surface of the solid-state image pickup device, and electric charges proportionate to the amount of light corresponding to each picture element of the optical image accumulate in each optical device on the image pickup surface. The electric charges accumulated in each optical device are converted into an electrical signal. In the end, the signal is reproduced on the monitor display as an X-ray image. As a result, the blackening degree of each picture element of the X-ray image on the display is nearly proportionate to the penetrated X-ray dose which has stimulated each picture element on the fluorescent surface.

The X-ray image detecting device of present invention is characterized in that the X-ray intensity detecting element is disposed adjacent to the X-ray fluorescent element in the outer casing thereof, the X-ray detection intensity by using the X-ray intensity detecting element is detected correlatively to the detection intensity by using the CCD device, the X-ray intensity detecting element electrically detects the target object or the X-ray penetrated the vicinity of the object and generates an output signal proportionate to the intensity of the X-rays. This output is integrated to calculate the X-ray dose irradiated during the X-ray radiation period. When the X-ray dose is compared with and becomes equal to the preset X-ray dose required to obtain the optimum image quality, X-ray radiation is stopped. Consequently, proper X-ray images having an appropriate blackening degree can be obtained on the display.

Moreover, since at least the X-ray incident surface of the outer casing of the device of the present invention is made of a soft X-ray absorbing material, the high-energy X-rays such as the specific X-rays, which have penetrated the tooth section and its ambient tissues, also penetrate the soft X-ray absorbing material and are projected to the fluorescent surface. However, the scattered X-rays are absorbed by the soft X-ray absorbing material and cannot reach the fluorescent surface, preventing noise signals from generating. As a result, the reproduced X-ray image becomes clear.

As the soft X-ray absorbing material, a single aluminum plate or an appropriate lamination of rare earth metals and plastic plates is used.

The thickness of the material is roughly determined experimentally considering the intensity of the irradiated X-rays and the energy distribution of the X-ray source. The appropriate thickness of the aluminum plate is in the range of 0.5 to 5 mm in the case of a practical dental X-ray photographing apparatus.

If the surfaces on one end side of the glass fiber bundles are flat surfaces nearly perpendicular to the cores of the glass fiber filaments and joined to the fluorescent surface, the resolution of the optical image is not reduced when the optical image on the fluorescent surface is transmitted to the image pickup surface of the CCD device. In particular, when the surfaces on the other end side of the glass fiber bundles are flat surfaces nearly perpendicular to the cores of the glass fiber filaments and joined to the image pickup surface of the CCD device, the resolution of the image is not reduced even when the optical image projected to the image pickup surface of the CCD device is reproduced on the monitor as an X-ray image, and thus the obtained image is made clear.

Moreover, by forming the rear surface section of the container located in the X-ray radiation direction from the X-ray fluorescent element so that the section includes an X-ray shut-off material, the X-rays penetrating behind the device can be shut off and X-ray exposure to a human body can be reduced during treatment.

The details of the present invention will be described below referring to the accompanying drawings.

DETAILED DESCRIPTION OF THE INVENTION

Figure 1A:
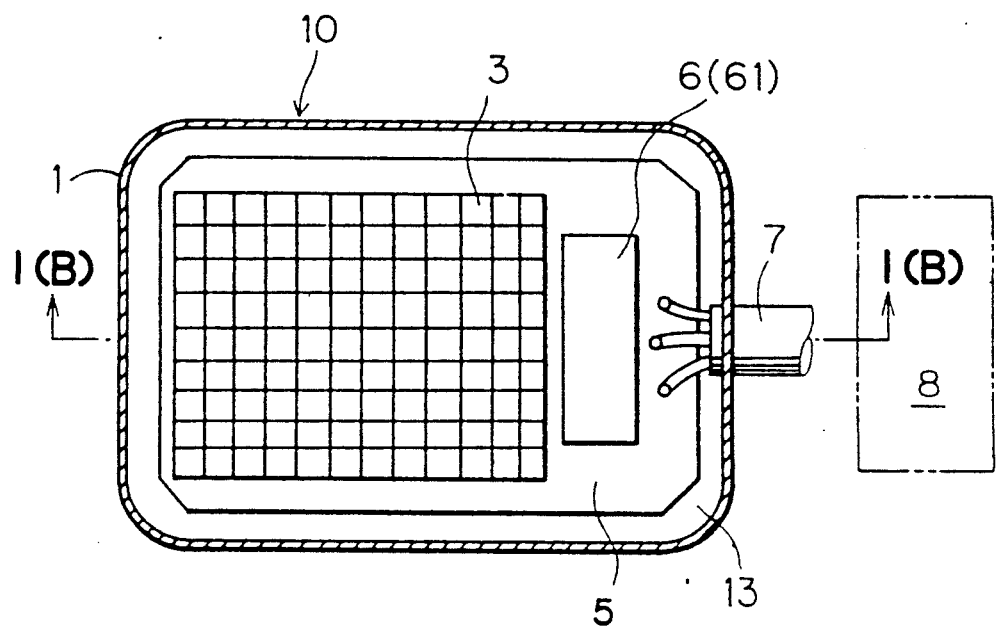
FIG. 1(A) is a transverse sectional view illustrating an example of a dental X-ray image detecting device, equipped with an X-ray intensity detecting element, of the present invention.
Figure 1B:
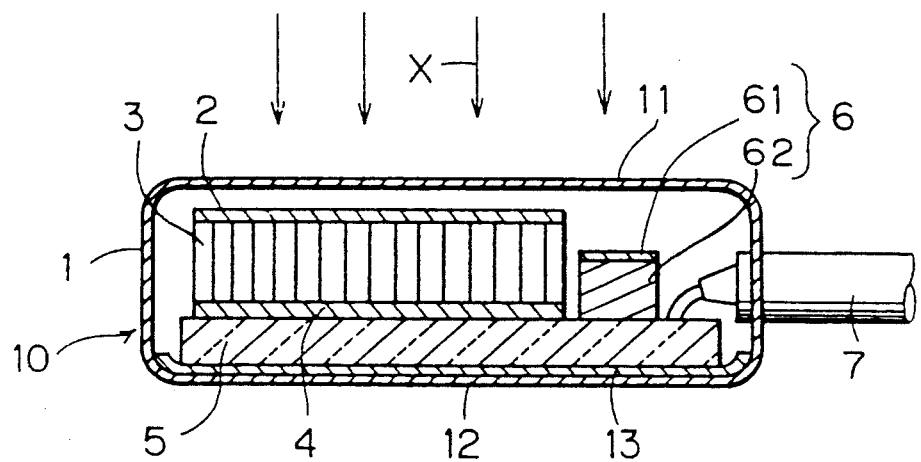
FIG. 1(B) is a vertical sectional view taken on line I—I of FIG. 1(A)

Referring to FIGS. 1(A) and 1(B), in a container 1, a ceramic substrate 5, on which a set of X-ray image sensor components is mounted, is secured to the inner bottom section of the container (the inner surface on the side opposite to the X-ray incident direction) via an X-ray shield material made of a lead plate.

On the ceramic substrate 5, a CCD device 4 having a shape of a chip is mounted. To the image pickup surface of the CCD device 4, the surfaces on one end side of the glass fiber bundles 3 are connected. The surfaces on the other end side of the glass fiber bundles 3 are connected to the fluorescent surface of an X-ray fluorescent element 2. This example has three layers comprising the CCD device 4, the glass fiber bundles 3 and the X-ray fluorescent element 2. Both the optical end surfaces of the glass fiber bundles 3 are flat surfaces nearly perpendicular to the cores of the glass fiber filaments and are joined to the fluorescent surface and the image pickup surface of the CCD device 4. The X-ray fluorescent element 2 is irradiated by the X-rays having penetrated the front section 11 of the container or casing 1 and emits light to produce a fluorescent image. The image is transmitted to the glass fiber bundles 3 and converted into an electrical signal on the image pickup surface of the CCD device 4. The CCD device 4 is connected to a control unit 8 located outside the detecting device via a cable 7 including lead wires 71 as shown in FIGS. 3 and 4.

An X-ray intensity detecting element 6 is secured to the ceramic substrate 5, adjacent to the fluorescent element 2 of the X-ray image sensor and beside the CCD device 4 (having a shape of chip). The X-ray intensity detecting element 6 comprises an optical detecting device 62 (phototransistor) and an X-ray fluorescent element 61 coated on the light receiving surface of the optical detecting device 62. The top surface of the X-ray fluorescent element 61 is rectangular and disposed parallel to the top surface of the fluorescent element 2. The X-rays which have penetrated the vicinity of a target tooth further penetrates and stimulates the X-ray fluorescent element 61 so that the fluorescent element 61 emits light. By using the emitted light, the light detecting device 62 generates an electrical signal, the level of which is proportionate to the intensity of the light. The signal is then transmitted to the control unit 8 outside the detecting device via the cable 7 including lead wires 71.

In order to generate a signal representing the average value of the irradiated X-ray intensity at the fluorescent element 2, the X-ray intensity detecting element 6 is disposed adjacent to the fluorescent element 2 of the X-ray image sensor. Furthermore, in order to generate a signal indicating the average value of the X-ray intensity inside a certain area, the X-ray fluorescent element 61 has a photosensitive area larger than a certain size.

Figure 2A:
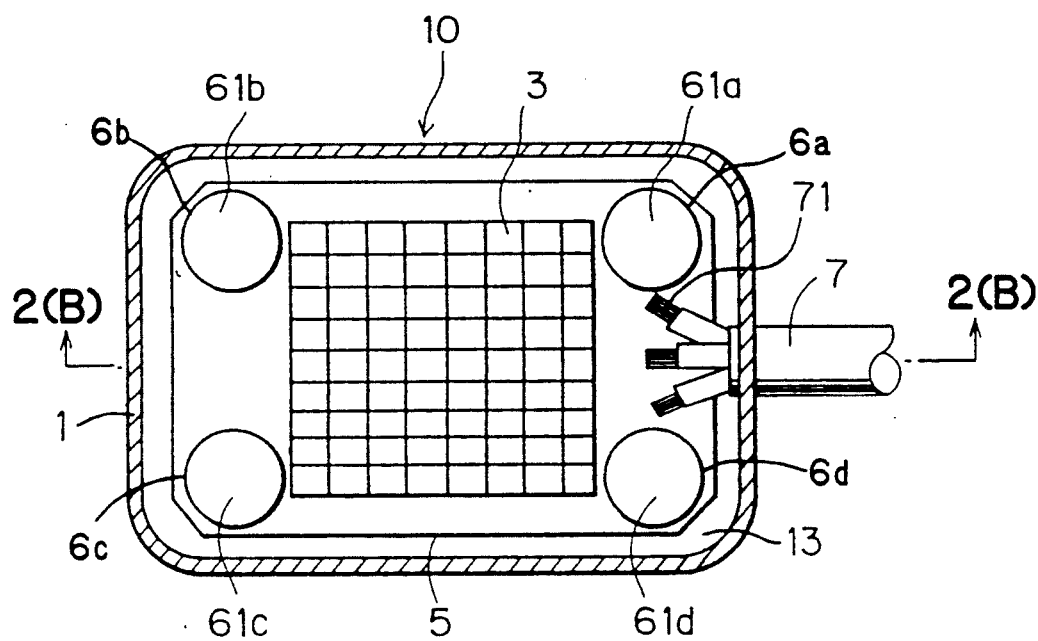
FIGS. 2(A) and 2(B) are transverse and vertical sectional views respectively, similar to FIGS. 1(A) and 1(B), illustrating another example of the present invention.
Figure 2B:
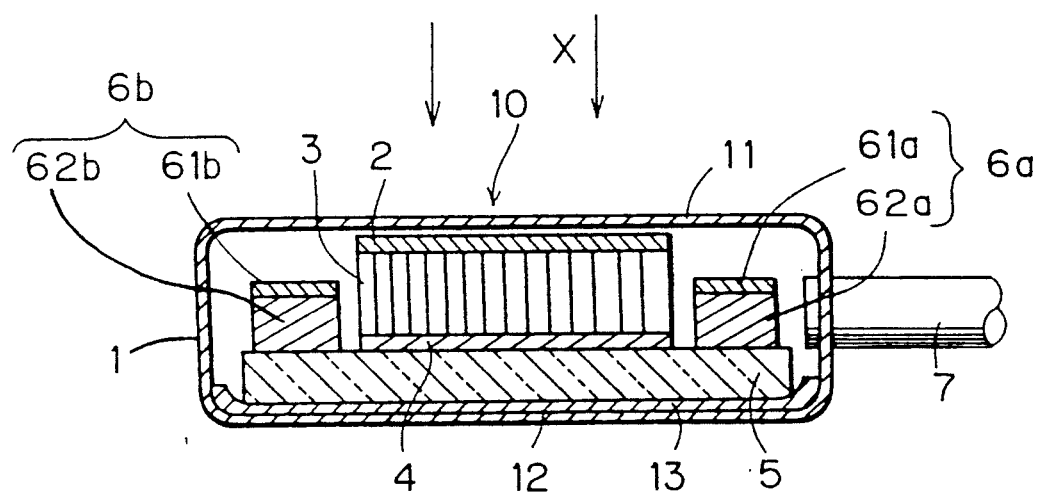

FIGS. 2(A) and (B) are sectional views of another example of an X-ray image detecting device of the present invention. In this example, four X-ray intensity detecting elements 6a, 6b, 6c and 6d are disposed at the four outside corners of the X-ray image sensor. Each of the detecting elements 6a, 6d comprises respectively light emitting elements 61a-61d and light detecting devices 62a-62d. By dividing the X-ray intensity detecting element 6 into four elements as described above, the average intensity of the X-rays entered the fluorescent element 2 of the X-ray image sensor is obtained and utilized. The electrical signal outputs from the X-ray intensity detecting elements 6a, 6b, 6c and 6d are simply added for example, then input to the above-mentioned integrating circuit to obtain the average X-ray dose data.

Figure 3A:
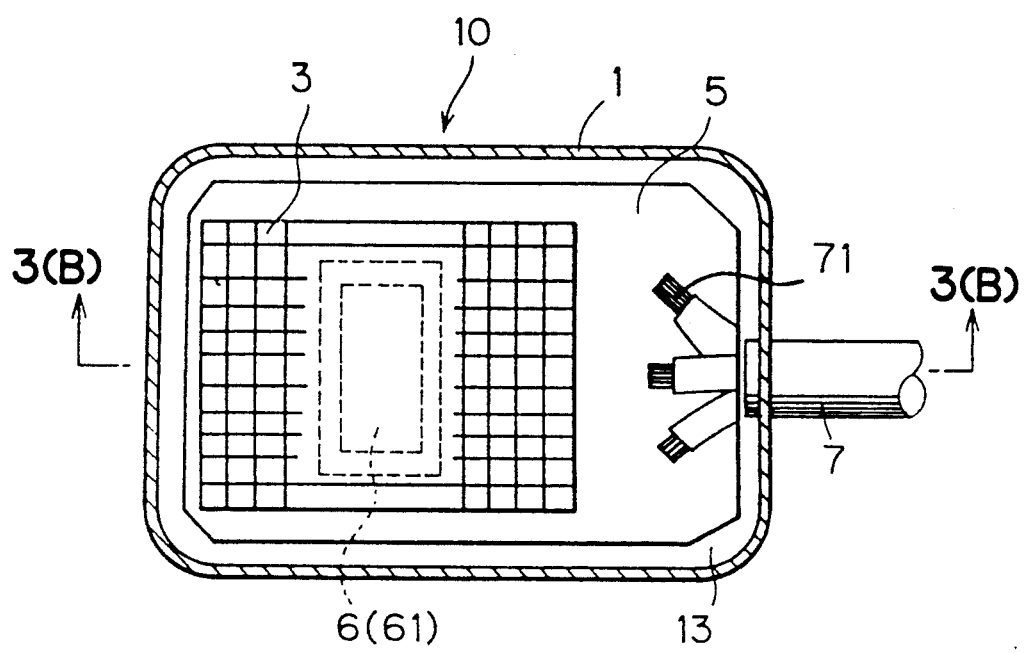
FIGS. 3(A) and 3(B) are transverse and vertical sectional views respectively, similar to FIGS. 1(A) and 1(B), illustrating a third example of the present invention.
Figure 3B:
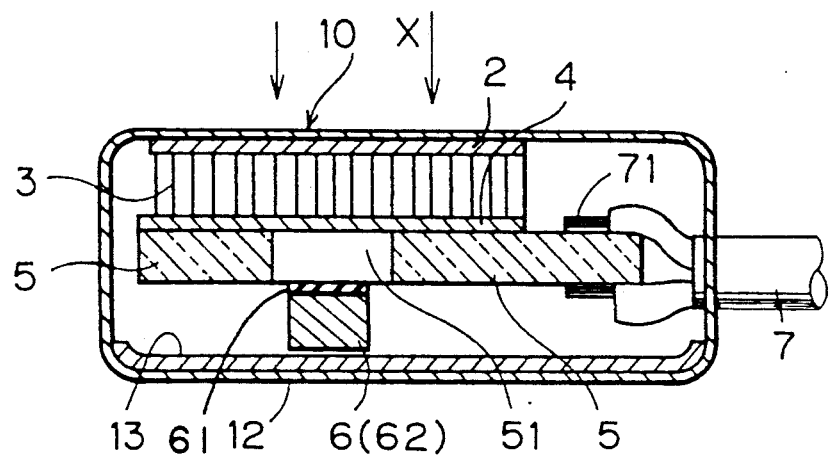
Figure 4:
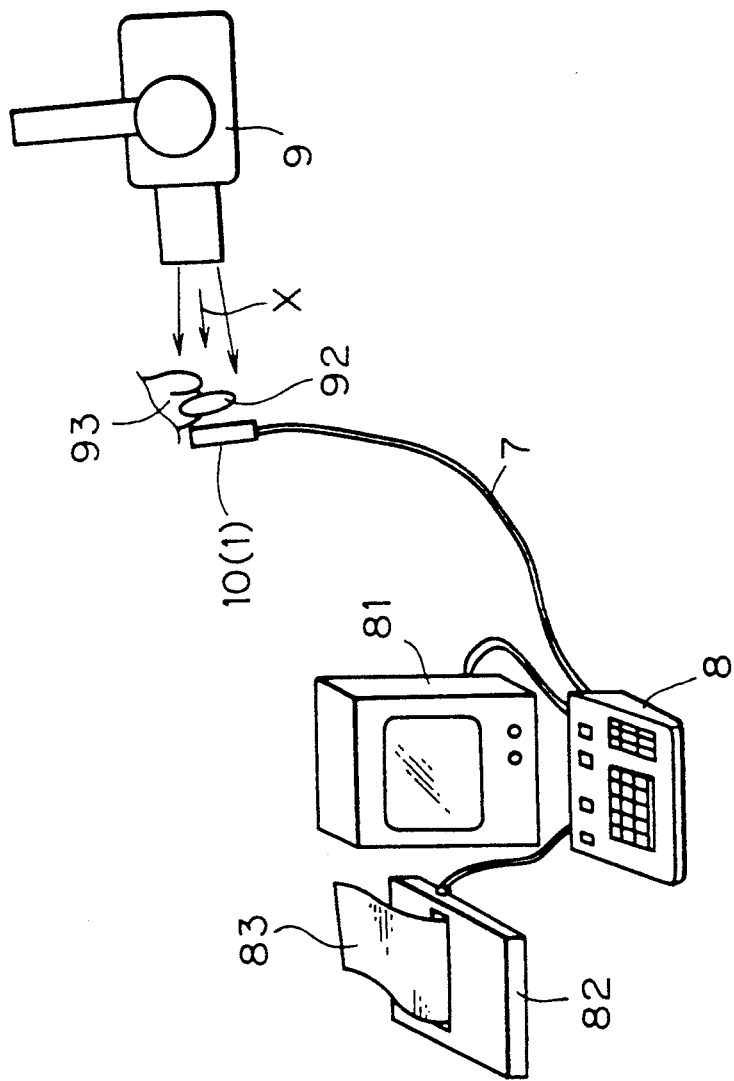
FIG. 4 is an X-ray photographing system configured by using the dental X-ray image detecting device of the present invention.

FIGS. 3(A) and (B) are sectional views of a third example of an X-ray image detecting device, wherein the X-ray intensity detecting element 6 is disposed adjacent to the opening 51 provided at a nearly central section of the ceramic substrate 5 for the X-ray image sensor and placed just under the CCD device 4. Since the X-rays entering the X-ray intensity detecting element 6 have penetrated the fluorescent element 2 of the X-ray image sensor and the CCD device 4, the penetrated X-ray dose at the nearly central section of the X-ray image can be measured, thereby increasing the reliability of the X-ray exposure time setting.

In the X-ray image detecting device, the X-ray image sensor with the X-ray intensity detecting element 6 is housed in the outer container 1. The front section 11, that is, the X-ray incident side, and the side sections of the container 1 are made of an aluminum plate. This aluminum plate is joined hermetically to the bottom section 12 of the above-mentioned container 1. Since this aluminum-plate front section 11 of the container 1 functions as a soft X-ray absorbing material, the low-energy scattered X-rays generated when the X-rays from the X-ray source penetrate a tooth area 93 such as a jaw bone including a tooth 92 and soft tissues are absorbed by the aluminum plate and almost prevented from reaching the CCD device 4. On the contrary, the main X-rays having penetrated the tooth area 93 penetrate the wall of the aluminum-plate container 1 and are projected to the fluorescent element 2 of the X-ray image sensor and the X-ray intensity detecting element 6.

FIG. 4 shows an application example of the dental X-ray image detecting device 10 of the present invention. An image signal is reproduced as an image on the monitor display 81 by the control unit 8 connected from the container 1 of the detecting device 10 via the cable 7. The image is then printed on paper 83 by a printer 82 as necessary.

With this configuration of the application example, when the X-rays from a compact X-ray generator 9 are irradiated to the target tooth 92 while the detecting device 10 is held behind the target tooth 92 in the mouth to be X-ray photographed, the X-ray penetration image of the tooth area 93 including the tooth 92 is indicated on the monitor display 81.

The control unit 8 includes an integrating circuit which integrates the output signal from the X-ray intensity detecting element 6 with respect to time, a comparison circuit which compares the integrated value with a preset value, and a control circuit which shuts off the anode current of the X-ray tube. Once the X-ray penetration dose appropriate for the analysis of the X-ray image of the tooth area 93 has been preset in the comparison circuit, when the X-ray penetration dose detected by the X-ray intensity detecting element 6 during X-ray photographing and subjected to integral calculation with respect to X-ray radiation time using the integrating circuit becomes equal to the preset X-ray penetration dose, the control circuit shuts off the anode current of the X-ray tube. At this shut-off time, the image signal stored in the CCD device 4 or in the storage device of the control unit 8 is reproduced as an X-ray image on the monitor display 81.

Instead of a solid-state optical device with a wide fluorescent surface, a solid-state device which directly responds to X-rays without using any fluorescent surface can be used as the X-ray intensity detecting element 6 of the X-ray image detecting device of the present invention. Furthermore, the amplifying and integrating circuits for processing the output from the X-ray intensity detecting element 6 can be mounted together with the X-ray intensity detecting element 6 on the ceramic substrate of the X-ray image sensor.

In the X-ray image detecting device of the present invention, the X-ray intensity detecting element for detecting X-ray penetration intensity and for adjusting X-ray exposure is disposed adjacent to the X-ray fluorescent element for X-ray image detection. Because of this arrangement, the X-ray dose calculated by integrating the intensity signal of the X-ray intensity detecting element with respect to radiation time can be used to control the X-ray radiation time during X-ray photographing, that is, exposure time. As a result, the X-ray image on the monitor display has a proper image with a constant blackening degree at all times and is useful for medical diagnosis. Additionally, failures due to insufficient exposure during X-ray photographing can be eliminated, thereby significantly reducing the frequency of rephotographing and capable of decreasing the X-ray exposure dose to the patient to the minimum limit value required. The resolution of the X-ray image can be enhanced by joining the cores of the glass fiber filaments nearly perpendicular to the fluorescent surfaces of the X-ray fluorescent element. Besides, the quality of the X-ray image cannot be deteriorated by the soft X-rays scattered by the target object when at least the front surface section of the X-ray incident side of the container is made of a soft X-ray absorbing material. This undeteriorated quality of the image and the uniform image quality due to the above-mentioned exposure control can greatly enhance the clearness of the X-ray image. Furthermore, the X-rays penetrating behind the detecting device can be shut off by using the rear surface section of the container comprising an X-ray shield material, and X-ray exposure during treatment can be reduced.

We claim:

1. A dental X-ray image detecting device to be disposed in an inter-oral region behind a tooth to be photographed, wherein X-rays penetrating the tooth are converted into an optical image and the optical image is then converted into a digital signal to be reproduced on a monitor display, said dental X-ray image detecting device arranged such that an X-ray image sensor comprising a first X-ray fluorescent element, a solid-state image pickup device mounted on a surface of a fixture substrate and a plurality of optical fiber bundles for optically connecting a fluorescent surface of the X-ray fluorescent element to an image pickup surface of the image pickup device, is housed in an outer casing, said dental image detecting device further comprising an X-ray intensity detecting element secured to the surface of the fixture substrate, said detecting element comprising a photo detecting element and a second X-ray fluorescent element mounted on the photo detecting element, wherein cores of filaments of all of the glass fiber bundles are joined substantially perpendicular both to the fluorescent surface of the first X-ray fluorescent element and to the surface of the solid-state image pickup device, each of said bundles having a diameter substantially equal to one another, and a bottom section of said outer casing, located in the X-ray radiation direction from the X-ray fluorescent element, includes an X-ray shield material.

2. A dental X-ray image detecting device according to claim 1, wherein said X-ray intensity detecting element is secured to a top surface of the fixture substrate adjacent to the X-ray image sensor.

3. A dental X-ray image detecting device according to claim 1, wherein said X-ray intensity detecting element is secured to a bottom surface of the fixture substrate.

4. A dental X-ray image detecting device according to claim 1, 2 or 3 wherein at least a front surface section on an X-ray incident side of said casing comprises a soft X-ray absorbing material.

* * * * *